US00PP17736P2

(12) United States Plant Patent
Misato et al.

(10) Patent No.: US PP17,736 P2
(45) Date of Patent: May 15, 2007

(54) ***MANDEVILLA* PLANT NAMED 'SUNMANDECRIKIN'**

(50) Latin Name: ***Mandevilla* hybrid**
Varietal Denomination: Sunmandecrikin

(75) Inventors: Tomoya Misato, Shiga (JP); Yasuyuki Murakami, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 11/264,769

(22) Filed: Nov. 1, 2005

(51) Int. Cl.
*A01H 5/00* (2006.01)

(52) U.S. Cl. ..... Plt./232
(58) Field of Classification Search ..... Plt./232
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Mandevilla* plant named 'Sunmandecrikin', characterized by its upright and vigorous vining growth habit; glossy and narrowly elliptic leaves; freely branching and flowering habit; red-colored flowers with imbricate petals; and long flowering period.

1 Drawing Sheet

Botanical designation: *Mandevilla* hybrid.
Cultivar denomination: 'Sunmandecrikin'.

BACKGROUND OF THE INVENTION

The present Invention relates to a new and distinct cultivar of *Mandevilla* plant, botanically known as *Mandevilla* hybrid, and hereinafter referred to by the name 'Sunmandecrikin'.

The new cultivar is a product of a planned breeding program conducted by the Inventors in Higashiomi, Shiga, Japan. The objective of the breeding program was to develop new *Mandevilla* cultivars with glossy leaves and attractive flower form and coloration.

The new cultivar originated from a cross-pollination made by the Inventors in June, 2001 of the *Mandevilla* hybrid cultivar Sunmandeho, disclosed in U.S. Plant Pat. No. 11,556, as the female, or seed, parent with a proprietary *Mandevilla* hybrid selection identified as code number M38-1, not patented, as the male, or pollen, parent. The new cultivar was discovered and selected by the Inventors as a flowering plant within the progeny from this cross-pollination in a controlled environment in Higashiomi, Shiga, Japan.

Asexual reproduction of the new cultivar by terminal cuttings in Higashiomi, Shiga, Japan, since October, 2004, has shown that the unique features of this new *Mandevilla* are stable and reproduced true to type in successive generations.

SUMMARY OF THE INVENTION

Plants of the cultivar Sunmandecrikin have not been observed under all possible environmental conditions. The phenotype may vary somewhat with variations in environment such as temperature and light intensity without, however, any variance in genotype.

The following traits have been repeatedly observed and are determined to be the unique characteristics of 'Sunmandecrikin'. These characteristics in combination distinguish 'Sunmandecrikin' as a new and distinct cultivar:

1. Upright and vigorous vining growth habit.
2. Glossy and narrowly elliptic leaves.

3. Freely branching and flowering habit.
4. Large red-colored flowers with imbricate petals.
5. Long flowering period.

Plants of the new *Mandevilla* can be compared to plants of the female parent, the cultivar Sunmandeho. In side-by-side comparisons conducted in Higashiomi, Shiga, Japan, plants of the new *Mandevilla* differed from plants of the cultivar Sunmandeho in the following characteristics:

1. Plants of the new *Mandevilla* had longer leaves than plants of the cultivar Sunmandeho.
2. Plants of the new *Mandevilla* and the cultivar Sunmandeho differed in flower color as plants of the cultivar Sunmandeho had white-colored flowers.

Plants of the new *Mandevilla* can be compared to plants of the male parent, the proprietary selection identified as M38-1. In side-by-side comparisons conducted in Higashiomi, Shiga, Japan, plants of the new *Mandevilla* differed from plants of the male parent selection in the following characteristics:

1. Plants of the new *Mandevilla* had broader leaves than plants of the male parent selection.
2. Plants of the new *Mandevilla* were more tolerant to high temperatures than plants of the male parent selection.

Plants of the new *Mandevilla* can be compared to plants of the *Mandevilla* cultivar, 'Sunmandecos', disclosed in U.S. Plant Pat. No. 15,202. In side-by-side comparisons conducted in Higashiomi, Shiga, Japan, plants of the new *Mandevilla* differed from plants of the cultivar Sunmandecos in the following characteristics:

1. Plants of the new *Mandevilla* had longer lateral branches and longer internodes than plants of the cultivar Sunmandecos.
2. Plants of the new *Mandevilla* had narrower leaves than plants of the cultivar Sunmandecos.
3. Plants of the new *Mandevilla* had slightly smaller flowers than plants of the cultivar Sunmandecos.
4. Plants of the new *Mandevilla* and the cultivar Sunmandecos differed in flower coloration as plants of the cultivar Sunmandecos had light red purple-colored flowers.

5. Plants of the new *Mandevilla* flowered for a longer period of time than plants of the cultivar Sunmandecos.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Mandevilla*.

The photograph at the top of the sheet comprises a side perspective view of a typical flowering plant of 'Sunmandecrikin'.

The photograph at the bottom of the sheet is a close-up view of typical flowers of 'Sunmandecrikin'.

DETAILED BOTANICAL DESCRIPTION

In the following description, color references are made to The Royal Horticultural Society Colour Chart, 2001 Edition, except where general terms of ordinary dictionary significance are used.

Plants used for the aforementioned photographs and following description were about seven months old and grown in 15-cm containers in an outdoor nursery during the summer in Yokaichi, Shiga, Japan. During the production of the plants, day temperatures averaged 25° C. and night temperatures averaged 15° C.

Botanical classification: *Mandevilla* hybrid cultivar Sunmandecrikin.

Parentage:

*Female, or seed, parent.*—*Mandevilla* hybrid cultivar Sunmandeho, disclosed in U.S. Plant Pat. No. 11,556.

*Male, or pollen, parent.*—Proprietary *Mandevilla* hybrid selection identified as code number M38-1, not patented.

Propagation:

*Type.*—Terminal cuttings.

*Time to initiate roots.*—About two weeks at 20° C. to 25° C.

*Time to develop roots.*—About 40 days at 20° C. to 25° C.

*Root description.*—Thick, fibrous, fleshy; light brown in color.

*Rooting habit.*—Freely branching.

Plant description:

*Form.*—Perennial evergreen flowering plant typically commercially grown as an annual; twining vine; initially upright, then vining, requires support to maintain upright habit. Freely branching habit, about twelve lateral branches per plant. Vigorous growth habit.

*Lateral branches.*—Length: About 172.6 cm. Diameter: About 4.1 mm. Internode length: About 13.2 cm. Shape: Round in cross-section. Aspect: Initially upright, then twining and trailing, plants require support. Strength: Flexible, moderately strong. Texture: Smooth, glabrous. Color, developing stems: 144A. Color, mature stems: 174A.

*Foliage description.*—Arrangement: Alternate; simple. Length: About 12.3 cm. Width: About 4.7 cm. Shape: Narrowly elliptic. Apex: Acute. Base: Rotund. Margin: Entire. Texture, upper and lower surfaces: Pubescent. Luster, upper and lower surfaces: Glossy. Venation pattern: Pinnate; reticulate. Petiole length: About 1 cm. Petiole diameter: About 2 mm. Petiole texture, upper and lower surfaces: Smooth. Color: Developing foliage, upper surface: 144A. Developing foliage, lower surface: 144B. Fully expanded foliage, upper surface: 146A; venation, similar to lamina. Fully expanded foliage, lower surface: 146B; venation, similar to lamina. Petiole, upper and lower surfaces: 144A.

Flower description:

*Flower type and habit.*—Single salverform flower; flowers racemose; flowers face upright or outwardly. Flowers not persistent. Freely flowering, about four flowers per inflorescence.

*Natural flowering season.*—Early summer to late autumn in Japan; flowering continuous during this period.

*Flower longevity on the plant.*—About seven to ten days.

*Fragrance.*—None detected.

*Inflorescence height.*—About 17 cm.

*Inflorescence diameter.*—About 13 cm.

*Flowers.*—Appearance: Flared trumpet, corolla fused, five-parted; petals imbricate; flowers roughly star-shaped. Diameter: About 10.9 cm. Depth (length): About 7.5 cm. Tube length: About 5 cm. Tube diameter (distal): About 2.2 cm. Tube diameter (proximal): About 3.7 mm.

*Flower buds.*—Length: About 7.5 mm. Diameter: About 1.5 cm. Shape: Oblong. Color: 53B.

*Corolla.*—Arrangement/appearance: Single whorl of five petals, fused into flared trumpet; petals imbricate. Petal length: About 5 cm. Petal width: About 5.2 cm. Petal shape: Spatulate. Petal apex: Rounded. Petal margin: Entire; undulate. Petal texture, upper and lower surfaces: Smooth, glabrous; satiny. Color: Petal, when opening, upper surface: 46B. Petal, when opening, lower surface: 53C. Petal, fully opened, upper surface: 53B; towards the center, close to 53A. Petal, fully opened, lower surface: 53C. Throat: 26A. Tube: 53C.

*Sepals.*—Arrangement/appearance: Five per flower in a single whorl; fused star-shaped calyx. Length: About 4.7 mm. Width: About 2.1 mm. Shape: Roughly deltoid. Apex: Acute. Margin: Entire. Texture, upper and lower surfaces: Smooth, glabrous. Color, upper and lower surfaces: 144C; towards the apex, 182B.

*Peduncles.*—Length: About 5.2 cm. Diameter: About 2.1 mm. Angle: Mostly straight. Strength: Flexible, but strong. Texture: Smooth. Color: 144D.

*Pedicels.*—Length: About 2.2 cm. Diameter: About 2 mm. Angle: Mostly straight. Strength: Flexible, but strong. Texture: Smooth. Color: N199A.

*Reproductive organs.*—Stamens: Quantity/arrangement: Typically five; filaments fused to corolla; anthers, connivent. Anther shape: Lanceolate. Anther size: About 7 mm by 1 mm. Anther color: 16C. Pollen amount: Moderate. Pollen color: Close to 16C. Pistils: Quantity: Typically one. Stigma shape: Conical. Stigma color: 144B. Style length: About 1.5 cm. Style color: 144D. Ovary color: 144B.

*Seeds.*—Seed development has not been observed on plants of the new *Mandevilla*.

Disease/pest resistance: Plants of the new *Mandevilla* have not been noted to be resistant to pathogens and pests common to *Mandevilla*.

Temperature tolerance: Plants of the new *Mandevilla* have been observed to be tolerant to rain and wind and tolerant to temperatures from 4° C. to 35° C.

It is claimed:

1. A new and distinct cultivar of *Mandevilla* plant named 'Sunmandecrikin', as illustrated and described.

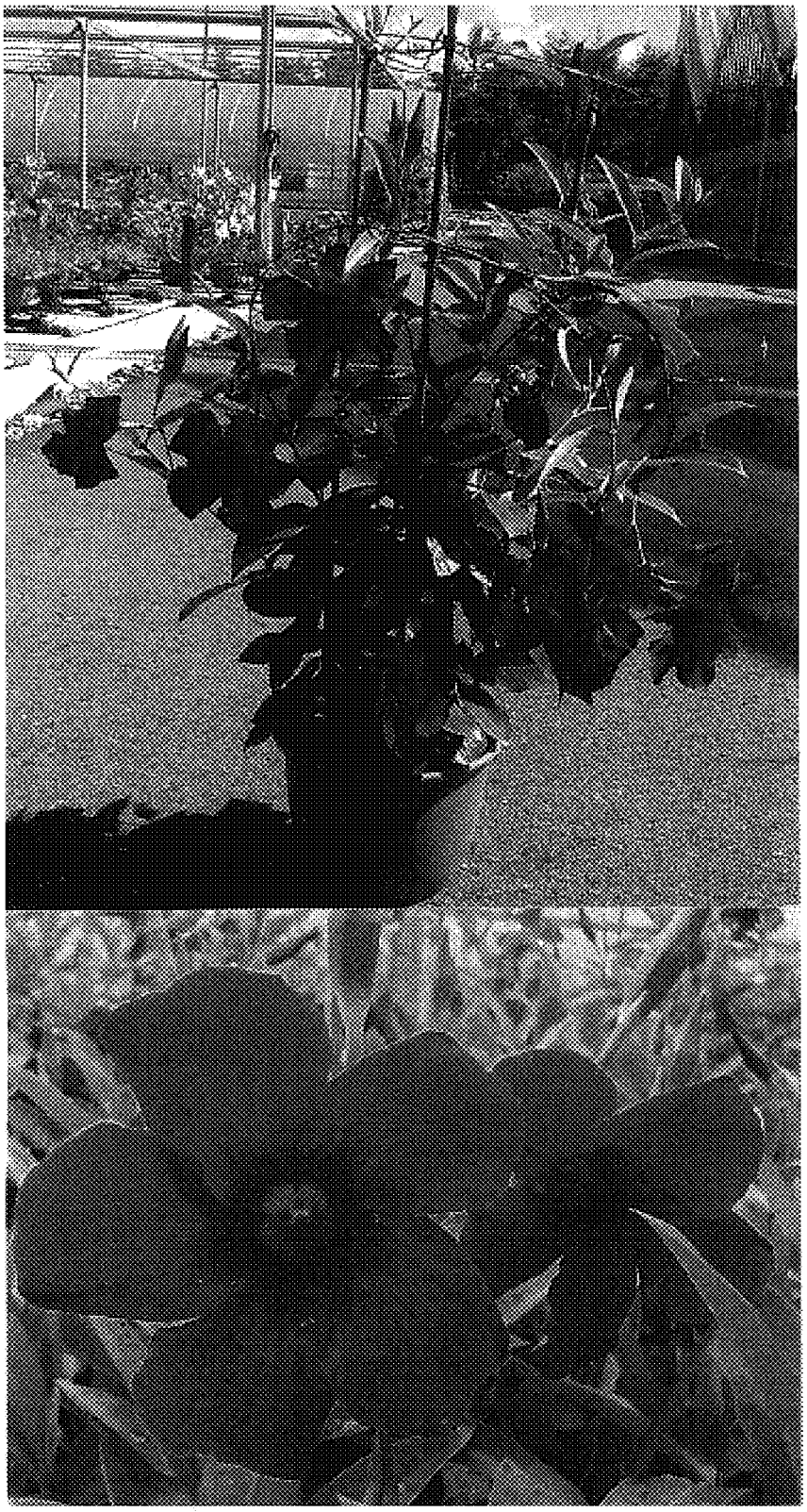

* * * * *